United States Patent
Messner-Rugova

(10) Patent No.: US 11,400,020 B2
(45) Date of Patent: Aug. 2, 2022

(54) MEDICINE CONTAINER FOR STORING AND PROVIDING AT LEAST TWO MEDICINE SUBSTANCES THAT CAN BE MIXED WITH ONE ANOTHER, AND METHOD FOR OPERATING A MEDICINE CONTAINER OF THIS TYPE

(71) Applicant: VETTER PHARMA-FERTIGUNG GMBH & CO. KG, Ravensburg (DE)

(72) Inventor: Fatbardha Messner-Rugova, Meckenbeuren (DE)

(73) Assignee: VETTER PHARMA-FERTIGUNG GMBH & CO. KG, Ravensburg (DE)

( * ) Notice: Subject to any disclaimer, the term of this patent is extended or adjusted under 35 U.S.C. 154(b) by 445 days.

(21) Appl. No.: 16/485,841

(22) PCT Filed: Feb. 15, 2018

(86) PCT No.: PCT/EP2018/053786
§ 371 (c)(1),
(2) Date: Aug. 14, 2019

(87) PCT Pub. No.: WO2018/149920
PCT Pub. Date: Aug. 23, 2018

(65) Prior Publication Data
US 2020/0054524 A1  Feb. 20, 2020

(30) Foreign Application Priority Data
Feb. 17, 2017 (DE) ................ 10 2017 202 607.3

(51) Int. Cl.
*A61J 1/20* (2006.01)
*A61M 5/24* (2006.01)
*A61J 1/06* (2006.01)

(52) U.S. Cl.
CPC ............ *A61J 1/2093* (2013.01); *A61J 1/062* (2013.01); *A61M 5/2422* (2013.01); *A61M 5/2448* (2013.01)

(58) Field of Classification Search
CPC ............ A61M 5/2066; A61M 5/31596; A61M 5/2422; A61M 5/2448; A61M 5/284; A61J 1/2093; A61J 1/062
See application file for complete search history.

(56) References Cited

U.S. PATENT DOCUMENTS 3,164,303 A    1/1965  Trautmann
3,326,215 A *  6/1967  Sarnoff ................ A61M 5/284
                                                    604/90

(Continued)

FOREIGN PATENT DOCUMENTS

EP    0328699 A1   8/1989
JP    S6148377 A   3/1986

(Continued)

OTHER PUBLICATIONS

Translation of Description of WO 84/01510A1, Verlier. Translated on espacenet.com on Dec. 31, 2021. (Year: 1984).*

(Continued)

*Primary Examiner* — Nathan R Price
*Assistant Examiner* — Melissa A Snyder
(74) *Attorney, Agent, or Firm* — Harness, Dickey & Pierce, P.L.C.; Stephen T. Olson

(57) ABSTRACT

A medicine container for medicine substances which can be mixed with one another includes a container body, a stopper and a mixing element. The container body has a first end with a stopper opening and a second end with a base having an outlet. The stopper is displaceable between the ends. A mixing chamber for receiving the medicine substances is delimited by a portion of an inner casing surface of the (Continued)

container body, a side of the stopper and the base. The mixing element can be disposed in the mixing chamber. The medicine container is adapted to discharge the medicine substances from the medicine container by displacement of the stopper in the direction of the outlet. The stopper is adapted to receive the mixing element at least partially by a recess. The invention further relates to a method for operating such a medicine container.

10 Claims, 2 Drawing Sheets

(56) References Cited

U.S. PATENT DOCUMENTS

| | | | | |
|---|---|---|---|---|
| 3,789,670 | A | * | 2/1974 | Rosenwald ......... B01F 11/0082 73/864.62 |
| 4,599,082 | A | | 7/1986 | Grimard |
| 4,874,381 | A | | 10/1989 | Vetter |
| 5,725,500 | A | * | 3/1998 | Micheler ................ A61J 1/062 366/130 |
| 8,092,421 | B2 | | 1/2012 | Seiferlein et al. |
| 10,292,749 | B2 | | 5/2019 | Shim |
| 2003/0163084 | A1 | | 8/2003 | Griffiths et al. |
| 2010/0262074 | A1 | | 10/2010 | Seiferlein et al. |
| 2012/0118139 | A1 | | 5/2012 | Seiferlein et al. |
| 2017/0143397 | A1 | | 5/2017 | Shim |

FOREIGN PATENT DOCUMENTS

| | | | | |
|---|---|---|---|---|
| JP | 2007117272 | A | | 5/2007 |
| JP | 2014200298 | A | | 10/2014 |
| RU | 2067004 | C1 | | 9/1996 |
| RU | 2130323 | C1 | | 5/1999 |
| RU | 2137509 | C1 | | 9/1999 |
| WO | WO-8401510 | A1 | * | 4/1984 .......... A61M 5/3243 |
| WO | WO-03053494 | A2 | | 7/2003 |
| WO | WO-2008151737 | A1 | | 12/2008 |
| WO | WO-2015199336 | A1 | | 12/2015 |

OTHER PUBLICATIONS

Search Report received for the Russian Patent Application No. 2019125849, dated Nov. 19, 2020, 2 pages.

Japanese Office Action in JP Application No. 2019-544015, dated Aug. 3, 2021.

Written Opinion and Search Report issued in corresponding International Application No. PCT/EP2018/053786, dated Aug. 29, 2019.

International Search Report (in English and German) and Written Opinion (in German) issued in PCT/EP2018/053786, dated May 30, 2018; ISA/EP.

* cited by examiner

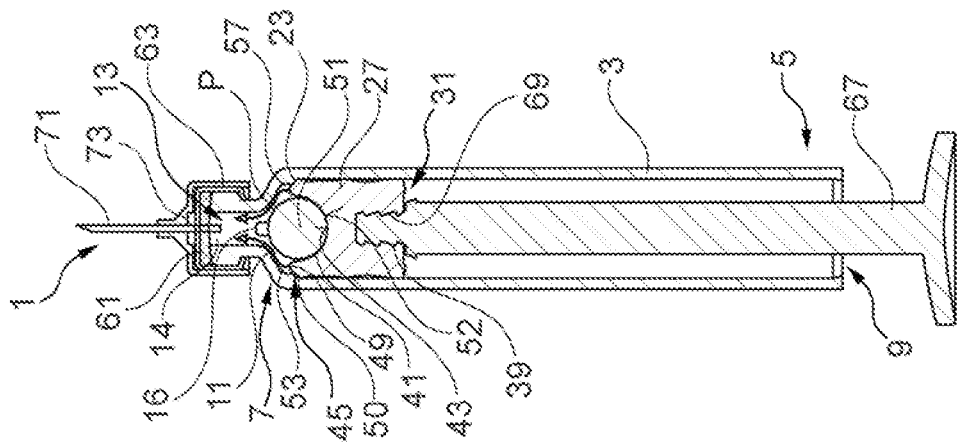
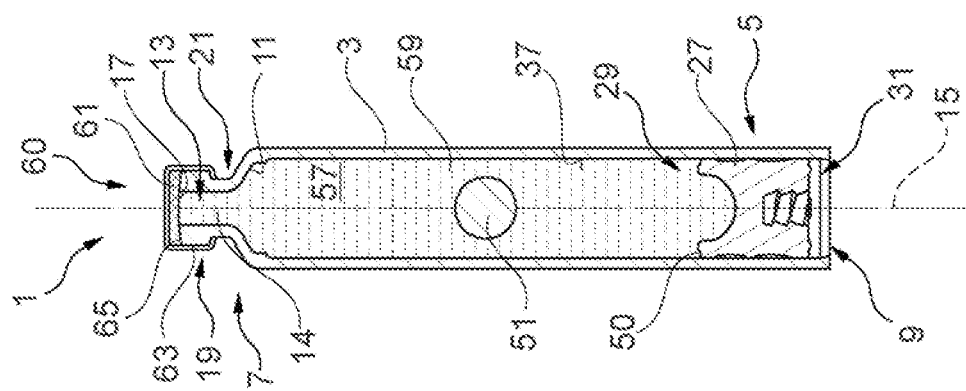
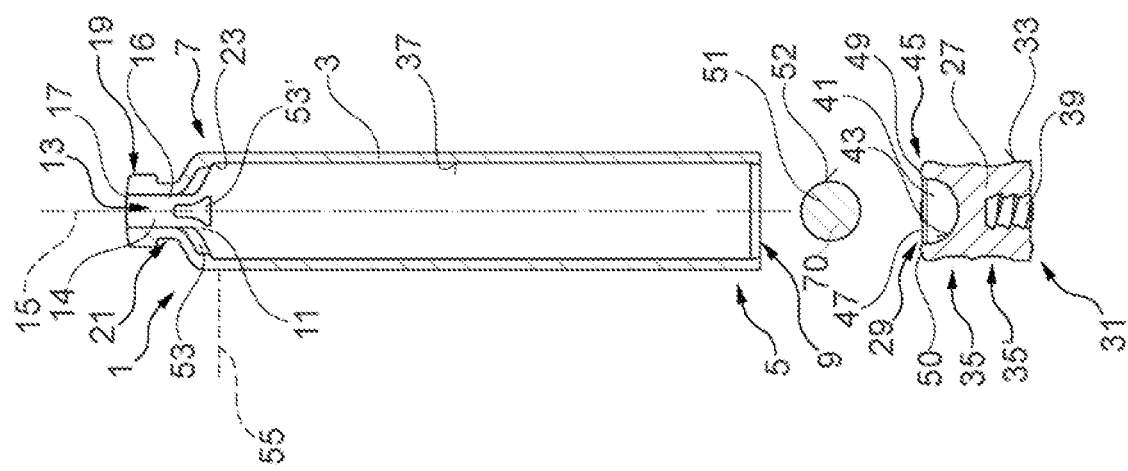

MEDICINE CONTAINER FOR STORING AND PROVIDING AT LEAST TWO MEDICINE SUBSTANCES THAT CAN BE MIXED WITH ONE ANOTHER, AND METHOD FOR OPERATING A MEDICINE CONTAINER OF THIS TYPE

CROSS-REFERENCE TO RELATED APPLICATIONS

This application is a 371 U.S. National Phase of International Application No. PCT/EP2018/053786, filed Feb. 15, 2018, which claims priority to German Patent Application No. 10 2017 202 607.3, filed Feb. 17, 2017. The entire disclosures of the above applications are incorporated herein by reference.

FIELD

The invention relates to a medicine container for storing and providing at least two medicine substances which can be mixed with one another and to a method for operating such a medicine container.

BACKGROUND

Medicine containers for storing and providing at least two medicines substances which can be mixed with one another and methods for operating such medicine containers are known. They are commonly used in conjunction with medicines having at least two phases and serve to mix the at least two phases prior to application thereof. Particularly for multiphase medicines present as coarsely dispersed systems which have a liquid with typically heterogeneously distributed particles therein, an air-free filling and storage in the medicine container is to be aimed at because of the prolonged shelf life. Furthermore, multiple application of multiphase medicines stored in a medicine container is increasingly sought. In particular, medicines in the form of suspensions, in particular heterogeneous compositions of liquid and finely divided solids, and as emulsions, especially two immiscible liquids which are distributed as very fine droplets, require effective mixing of the different phases of the medicine prior to administration thereof to ensure a uniform concentration of the phases for each application. For mixing such multiphase medicines, mixing elements are known which are disposed so as to be freely displaceable in a medicine container, wherein shaking of the medicine container displaces the mixing element relative to the medicine container and thereby promotes a mixing of the different phases of the medicine. It has been shown time and again that the mixing element is often too small and/or too light to effect a rapid and effective homogenization of the medicine. It has also been shown that an enlargement of the mixing element is frequently not possible without obstructing a discharging behavior of the medicine container, in particular with a high viscosity of the medicine stored therein. The discharging behavior of the medicine container is significantly worsened in so far as—with respect to the medicine container—a dead volume increases with increasing size of the mixing element, and thus an amount of the medicine which cannot be discharged from the medicine container increases as well. In addition, independent outflow of the medicine from the medicine container becomes more difficult with increasing viscosity. An effectively dead volume which is increased by a deteriorated discharging behavior leads to high costs due to the incomplete use of expensive medicine components. In addition, a dosing accuracy of the medicine container can be adversely affected.

SUMMARY

The object of the invention is therefore to provide a medicine container and a method of the type mentioned above such that the disadvantages mentioned here can be avoided.

To solve this problem, a medicine container is proposed for storing and providing at least two medicines substances which can be mixed together, the container having the features mentioned in claim 1. Thus, a medicine container is provided for storing and providing at least two medicine substances which can be mixed with one another, the container comprising a container body, a stopper and a mixing element. The container body has a first end and a second end opposite the first end. The container body has a stopper opening at the first end. Further, in the container body at the second end thereof, a base is provided with an outlet. The stopper, which is insertable into the container body through the stopper opening, is displaceable in the container body along a longitudinal axis thereof between the first and the second end. A mixing chamber for receiving the at least two medicine substances is delimited by a portion of an inner casing surface of the container body, a side of the stopper facing the outlet, and the base. The mixing element can be disposed in the mixing chamber. The medicine container is adapted to at least partially discharge the at least two medicine substances received in the mixing chamber from the medicine container through the outlet by displacing the stopper in the direction of the outlet. By means of a recess formed on the side of the stopper facing the outlet, the stopper is adapted to receive the mixing element at least partially, especially when the stopper is disposed at the second end of the container body. In particular, when the stopper is positioned at the second end of the container body, the stopper at least partially receives the mixing element by means of the recess. The medicine container has advantages over the prior art. Since the stopper at least partially receives the mixing element using the recess formed on the side of the stopper facing the outlet when the stopper is positioned at the second end of the container body, a discharge behavior of the medicine container is improved by the fact that a dead volume of the at least two medicine substances, in particular mixed with each other, is significantly reduced. In this way, a waste of expensive substances and associated cost disadvantages are minimized or even eliminated. In addition, a miscibility of suspensions and emulsions, in particular coarsely dispersed systems, is improved by preferably using a sufficiently large mixing element. In particular, because of the improved miscibility, a multiple use of a medicine prepared by mixing the at least two medicine substances is possible, wherein a constant concentration of the at least two medicine substances is ensured for each respective application. Such multiple use of the medicine is thus possible with a single pen. By means of the medicine container according to the invention, an improved miscibility of the medicine is made possible, in particular in the case of an air-free dispensing thereof, wherein a shelf life of the medicine is significantly increased. Furthermore, by means of the medicine container according to the invention, sparingly soluble lyophilizates in particular can be rapidly and effectively dissolved in a suitable solvent.

In particular, the at least two medicine substances give a coarsely dispersed system, with particles having a diameter of greater than 1 μm in particular being distributed heterogeneously in a liquid. Alternatively or additionally, the at least two medicine substances form a suspension, wherein in particular liquid and finely divided solids form a heterogeneous substance mixture, or an emulsion, wherein in particular two immiscible liquids are distributed as very fine droplets into one another.

The fact that the at least two medicine substances are "immiscible" here means in particular that the medicine substances do not form a homogeneous phase with one another, and in particular preferably have at least one miscibility gap in the phase diagram of the substance mixture. In contrast to this, the term "mixing" is understood to mean that a homogenization in the sense of the as uniform as possible of a distribution of the medicine substances in each other is sought. In this sense, immiscible substances, especially immiscible liquids, are intermixable by, for example, slurrying a suspension and thus solid particles distributed as homogeneously as possible in a liquid, for example or by mixing separate liquids in two separate phases so that an emulsion results which has as homogeneous a distribution of a liquid in the other liquid as possible.

The mixing element can be displaced in the mixing chamber, in particular independently of the stopper and/or outside the stopper, for the purpose of mixing the medicine substances. Particularly preferably, the mixing element is displaceable independently of the stopper and outside of the stopper in the mixing chamber. This is the case at least until the stopper is disposed at the second end of the container body in such a way that it receives the mixing element at least partially, in particular in the recess formed on the side facing the outlet.

The container body is preferably formed as a hollow body, which is in particular tubular. Preferably, the container body is formed of glass or plastic. Particularly preferably, the medicine container is designed as a syringe or as a carpule, in particular for use in a pen.

The stopper preferably comprises a flexible material, in particular a plastic, or consists of such a material. In particular, it is designed to prevent a fluid, in particular a gas or a liquid, from flowing between an outer casing surface of the stopper and the inner casing surface of the container body or through the stopper itself when made in the container body.

Preferably, the stopper has—for example in an embodiment of the medicine container as a syringe—an inner threading on a side thereof facing away from the outlet, into said threading preferably a piston with a corresponding external thread can be screwed. A displacement of the stopper along the longitudinal axis of the container body between the first and the second end is preferably effected by means of the piston, wherein the piston in particular reaches through the stopper opening during a displacement of the stopper.

Alternatively, the stopper—for example in an embodiment of the medicine container as a carpule, in particular for a pen—has an inner threading on the side thereof facing away from the outlet. In particular, a pressure force is then applied to the stopper by means of a piston on the side of the stopper facing away from the outlet, preferably via a die disposed on the piston, wherein a displacement of the stopper is effected along the longitudinal axis of the container body between the first and the second end.

The mixing element preferably comprises a material or consists of a material which is designed to be inert relative to the medicine stored by means of the medicine container according to the invention, in particular relative to the at least two medicine substances which can be mixed with one another. In particular, the mixing element comprises a material or consists of a material which does not lead to an impairment of the stored medicine, in particular of the at least two medicine substances which can be mixed with one another. The mixing element preferably has a different density from the at least two medicine substances, in particular a higher density, wherein in particular by means of fewer shaking movements an effective homogenization of the medicine is effected. Furthermore, the mixing element preferably has a certain geometric shape and/or certain dimensions, which in particular allow homogenization of the medicine by means of less shaking movements.

Preferably, the outlet can be closed in a fluid-tight manner by means of a closure device, the outlet being closed in a fluid-tight manner for storing the at least two medicine substances in particular. Preferably, the closure device has a septum which can be punctured, in particular by means of an injection needle, so that it is possible to discharge the at least two medicine substances, in particular mixed together, from the medicine container through the injection needle.

In particular, for purposes of storing the at least two medicine substances, the mixing chamber is fluid-tightly bounded by the portion of the inner casing surface of the container body, the outlet-facing side of the stopper and the base, wherein the medicine can be discharged from the medicine container via the outlet, in particular by applying an injection needle which penetrates the closure device. The mixing element can be displaced inside the mixing chamber, preferably along the longitudinal axis of the container body and in particular can be displaced in the radial direction—relative to the longitudinal axis—freely and independently separate from the stopper, when the stopper is not disposed at the second end of the container body. In this way in particular, an effective and rapid mixing of the two medicine substances by can be effected by shaking the medicine container.

By displacement of the stopper in the direction of the outlet, the at least two medicine substances received in the mixing chamber are at least partially discharged from the medicine container through the outlet, whereby in particular a closure device closing the outlet releases a discharge for this purpose, for example by piercing a septum by means of an injection needle.

When in a position at the second end of the container body, the stopper at least partially receives the mixing element by means of the recess, wherein the stopper at least partially reaches over the mixing element. The mixing element is then at least partially in the recess of the stopper. Preferably, the recess is aligned with the outlet on the stopper. Particularly preferably, the recess is formed in a central region of the stopper—with respect to the longitudinal axis of the container body. Particularly preferably, the outlet is disposed in a central region of the base—with respect to the longitudinal axis of the container body—, wherein particularly preferably the recess and the outlet are formed in alignment with each other.

One embodiment of the medicine container is preferred, which is characterized in that a shape of an outer surface of the stopper in the region of the recess is adapted to a shape of an outer surface of the mixing element such that no cavity remains between the outer surface of the stopper in the region of the recess and the outer surface of the mixing element when the stopper reaches over the mixing element to a maximum extent. In principle, the stopper's reaching over the mixing element can be effected at every position of the stopper in the container body. It is crucial that the mixing element is maximally overlapped no later than when the displacement of the stopper in the direction of the outlet by means of the recess has reached the position of the stopper at the second end of the container body. Preferably, jamming of the mixing element due to the stopper in the recess is prevented at a maximum overlap of the mixing element by the stopper by means of the recess. This in particular prevents the mixing element becoming jammed in the recess before the stopper reaches the second end of the container body during a displacement of the stopper for discharging the at least two medicine substances. By preventing a cavity between the outer surface of the stopper in the region of the recess and the outer surface of the mixing element overlapped by the stopper, a dead volume of the at least two medicine substances can advantageously be significantly reduced.

An embodiment of the medicine container is preferred which is characterized in that the stopper partially rests on the base in a position thereof at the second end of the container body. Preferably, no cavity remains between a region of the stopper lying on the base and the base so that a dead volume of the at least two medicine substances is significantly reduced.

An embodiment of the medicine container is preferred which is characterized in that at least a first groove which opens into the outlet is made in the base. Preferably, when the stopper is located at the second end of the container body, the at least two medicine substances can be discharged from the medicine container through the outlet at least by way of the at least one first groove. In a preferred embodiment of the medicine container, four first grooves are made in the base, each opening to the outlet. In principle, a different number of first grooves can also be made in the ground, wherein good discharging behavior from the medicine container is ensured with respect to the at least two medicine substances by means of the at least one first groove. The number of first grooves, as are the shape and/or dimensions thereof, are matched to the at least two medicine substances, in particular to a viscosity thereof. Thus, this ensures good discharge in an advantageous manner by means of at least one first groove, wherein when the stopper is located at the second end of the container body the outlet is prevented from closing due to the stopper either completely or to such an extent that a discharge of the at least two medicine substances according to a proper use of the medicine container is hindered. In particular, the design of the base according to the invention, with the at least one first groove, preferably causes the at least two medicine substances to flow past the mixing element.

In a preferred embodiment of the medicine container four first grooves are made in the base, disposed in particular at the same distance from each other on the base and extending substantially radially outward from the outlet, which in particular is centrally disposed. In each case, a first end of the first grooves opens into the outlet, wherein a second end ends in each case in the region of the inner casing of the container body.

By means of the at least one first groove, the discharge behavior of the medicine container can be ensured in an advantageous manner even with a high viscosity of the medicine, wherein a number and dimensions of the first grooves are in particular matched to the properties of the at least two medicine substances, in particular the viscosity thereof, such that an increase in the dead volume due to an unnecessarily high number of first grooves and/or an unnecessarily large dimensioning of the first grooves is avoided. In particular, good discharge behavior in conjunction with a reduced dead volume can be ensured in an advantageous manner. In particular, good discharge behavior is ensured even when the medicine container is in a position in which the outlet points vertically downward, wherein in particular the mixing element rests at the second end of the container body during the entire displacement of the stopper in the direction of the outlet. Good discharge behavior can be ensured by means of the at least one first groove even in the particular case that the mixing element has large dimensions relative to the container body.

An embodiment of the medicine container is preferred which is characterized in that at least one second groove is made in the outer surface of the mixing element. Preferably, when the stopper is located at the second end of the container body the at least two medicine substances can be discharged from the medicine container through the outlet at least by way of the at least one second groove. The at least one second groove preferably has a shape which enables a safe discharge of the at least two medicine substances with the smallest possible dead volume. In a preferred embodiment of the medicine container, a plurality of bumps are placed on the outer surface of the mixing element, wherein at a position of the stopper at the second end of the container body the at least two medicine substances can be discharged from the medicine container through the outlet at least by way of the channels formed by the bumps between the outer surface of the mixing element and the base. The discharge behavior of the medicine container can be improved in an advantageous manner by means of the suitably-shaped outer surface of the mixing element, in particular by means of the at least one second groove, wherein at the same time effective mixing is ensured, in particular by means of the mixing element and a particular minimized dead volume.

It should be noted here that the at least one second groove and/or the bumps can replace the at least one first groove. However, it is also possible to provide the at least one second groove and/or the bumps in addition to the at least one first groove. When the at least one first groove is implemented, in particular when the at least one second groove and/or the bumps are dispensed with, the smallest dead volume advantageously results, with a particularly large cost saving being realized.

An embodiment of the medicine container is preferred which is characterized in that the shape of the outer surface of the mixing element is matched to a shape of the base, that in a position of the stopper at the second end of the container body no cavity remains between the outer surface of the mixing element and the base in an area outside the at least one first and/or second groove and/or the bumps. Particularly preferably, at a position of the stopper at the second end of the container body the mixing chamber assumes a minimum volume, which in particular only results from the at least one first and/or second groove and/or the bumps. In this way, a dead volume of the medicine container is effectively minimized while at the same time an improved discharge behavior of the medicine container is realized.

An embodiment of the medicine container is preferred which is characterized in that the base is formed together with the outlet on a separate base element. Preferably, the separate base element is disposed on the container body at the second end thereof. Particularly preferably, the separate base element is fixedly disposed on the container body at the second end thereof. Particularly preferably, the separate base element is disposed at the second end of the container body in a fluid-tight manner on the container body. In a preferred embodiment, the container body is tubular at least at the second end thereof, wherein the separate base member at the second end of the tubular container body is in particular fluid-tightly connected to the container body. Preferably, the separate base element is made of plastic or comprises plastic.

In another preferred embodiment of the medicine container, the separate base element is disposed in the container body at the second end thereof, wherein it is prevented from falling out of the container body, in particular by means of a positive, locking, friction locking or material bonding connection.

Such a configuration may be advantageous because in particular a standardized separate base element can be used in a plurality of differently-shaped container bodies, resulting in cost advantages. Cost advantages can also be realized in that making the at least one first groove in the base on a separate base element can be realized more easily in terms of manufacturing technology than making the at least one first groove in a base formed integrally with the container body.

An embodiment of the medicine container is preferred which is characterized in that the mixing element is spherical. Preferably, the mixing element comprises a material or consists of a material which is selected from a group consisting of glass, steel, plastic and ceramic. Preferably, the mixing element has a coating. By means of such a mixing element, it is advantageously possible to uniformly mix coarsely-dispersed solutions, suspensions, in particular nanosuspensions, or poorly emulsified emulsions. Particularly preferably, the mixing element has a density which is higher than a density of the at least two medicine substances.

An exemplary embodiment of the medicine container is preferred which is characterized in that the mixing chamber is designed as a first chamber of a medicine container designed as a double-chambered carpule. Preferably, the stopper separates the mixing chamber from a second chamber disposed in the medicine container designed as a double-chambered carpule. Furthermore, the second chamber is preferably disposed between the first end of the container body and a side of the stopper facing away from the outlet. In particular, after introducing into the first chamber a phase of the medicine stored in the second chamber, preferably via a bypass channel in the inner casing surface of the container body, the at least two medicine substances are mixed together in the mixing chamber designed as a first chamber, wherein the two substances are mixed together in particular by shaking the medicine container by means of the mixing element. The medicine substances which are in particular mixed with one another can be at least partially discharged from the medicine container through the outlet by displacing the stopper in the direction of the outlet. Thus, an improved discharge behavior of the medicine container according to the invention can be achieved even when the container is designed as a double-chambered carpule.

In order to achieve the object, a method for operating a medicine container having a container body, a stopper and a mixing element is also proposed, said method comprising the features mentioned in claim 10. In the context of the method, in particular, the advantages that have already been explained in connection with the medicine container arise. In the method of the present invention, the stopper introduced into the container body is displaced along a longitudinal axis of the container body toward an outlet of the container body disposed at a second end of the container body, said displacement at least partially discharging at least two medicine substances which are mixable with each other in a mixing chamber of the medicine container from the medicine container through the outlet. By means of the stopper and at a position thereof at the second end of the container body, a mixing element disposed in the mixing chamber is at least partially received in a recess which is formed on a side of the stopper facing the outlet.

In particular, prior to a displacement of the stopper along the longitudinal axis of the container body in the direction of the outlet, the at least two medicine substances are mixed by shaking the medicine container, wherein by means of the back and forth displacement of the mixing element in the mixing chamber caused by the shaking separately and independently of the stopper, a mixing of the at least two medicine substances is caused or at least supported. In particular, a medicine containing the at least two medicine substances is homogenized by displacing the mixing element back and forth in the mixing chamber.

In a preferred embodiment of the method, a multiple, in each case at least partial, discharge of the at least two medicine substances from the medicine container is carried out. The outlet is preferably opened in each case prior to the at least partial discharge of the at least two medicine substances, for example by establishing a fluid connection between the mixing chamber and the surroundings of the medicine container by piercing an injection needle through a septum disposed at the outlet. In this case, the outlet is preferably closed again after an at least partial discharge, in particular if a further discharge is provided, so that the at least two medicine substances can be further stored safely and sustainably in the medicine container.

In particular, the mixing element can be at least partially held in the recess of the stopper before the stopper reaches the second end in a displacement of the stopper in the direction of the second end of the container body. It is crucial that the stopper at least partially receives the mixing element by means of the recess no later than when the stopper reaches the second end of the container body.

BRIEF DESCRIPTION OF THE DRAWINGS

The invention will be explained in more detail below with reference to the drawing. Shown are:

FIG. 1 shows a schematic illustration of a medicine container in an exploded cross section, FIG. 2 shows a schematic representation of the medicine container in a filled, closed state in a cross section, and FIG. 3 shows a schematic representation of the medicine container in an emptied state in a cross section.

DETAILED DESCRIPTION

Figure 4:
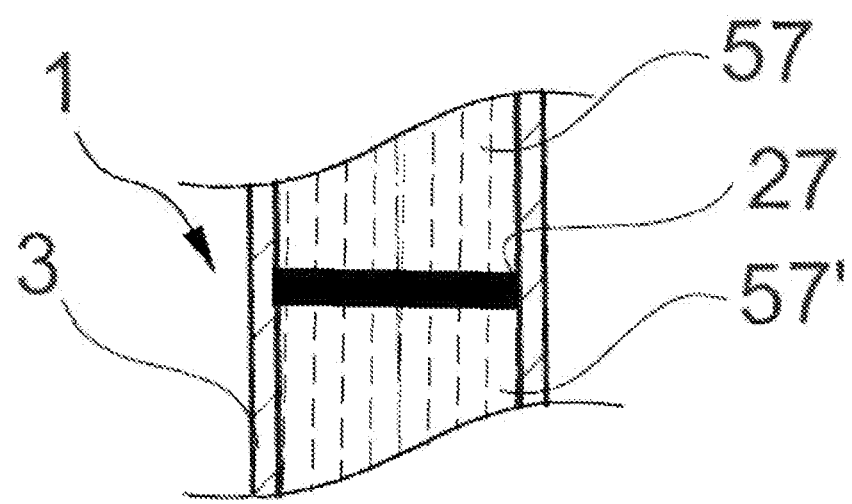
FIG. 4 is a simplified view of a portion of another medicine container designed as a double-chambered carpule including a first chamber and a second chamber.

FIG. 1 shows a schematic cross section of a medicine container 1 in an exploded view. The medicine container 1 is designed for storing and providing at least two medicine substances which can be mixed with one another. The medicine container 1 has a container body 3. Particularly preferably, the medicine container 1 is designed as a syringe or as a carpule, in particular for use in a pen, wherein the container body 3 comprises glass or plastic or consists of glass or plastic. The container body 3 has a first end 5 and a second end 7 opposite to the first end 5. At the first end 5, the container body 3 has a stopper opening 9. The container body 3 has at the second end 7 a base 11 with an outlet 13. The outlet 13 here has an outlet region 14 which extends along a longitudinal axis 15 of the container body 3 between an inner outlet opening 16, which here forms a kind of continuation of the base 11 in the region of the outlet 13, and an outer outlet opening 17. The outlet region 14 is surrounded radially by an extension 19 of the container body 3. The extension 19 has a constriction 21.

The container body 3 is preferably rotationally symmetrical. In the embodiment of FIG. 1, it is formed between the first end 5 and the second end 7 as a tubular hollow body with a substantially constant diameter. At the first end 5, a wall thickness of the container body 3 widens slightly inwards in the direction of the longitudinal axis 15. In this way, an outward displacement of a stopper introduced into the container body 3 is preferably made more difficult. In a region between the first end 5 and the second end 7, the wall thickness of the container body 3 is substantially constant. At the second end 7, the wall thickness of the container body 3 is designed to thicken inwardly in the direction of the longitudinal axis 15, wherein a circumferential projection 23 is formed in the container body 3. The base 11 is here funnel-shaped and extends—at its wide cross section—from the projection 23 to the inner outlet opening 16—at its narrow cross-section.

The medicine container 1 also has a stopper 27. The stopper 27 can be inserted into the container body 3 through the stopper opening 9. In the container body 3, the stopper 27 is displaceable along the longitudinal axis 15 between the first end 5 and the second end 7. The essentially cylindrically shaped stopper 27 has a side 29 facing the outlet 13 and a side 31 facing away from the outlet 13. A casing surface 33 extends between the side 29 facing the outlet 13 and the side 31 facing away from the outlet 13. The stopper 27 is likewise substantially rotationally symmetrical in shape, corresponding to the preferred rotationally-symmetrical design of the container body 3.

Between the side 29 facing the outlet 13 and the side 31 facing away from the outlet 13—along a longitudinal axis of the stopper 27—, the casing surface 33 has a shape which in the exemplary embodiment according to FIG. 1 comprises two constrictions 35, 35'. Outside dimensions of the stopper 27 are in particular matched to internal dimensions of the container body 3 such that the stopper 27 can be inserted via the stopper opening 9 into the container body 3 and such that it can displace in particular along the longitudinal axis 15 inside the container body 3. After the stopper 27 is introduced into the container body 3, an inner casing surface 37 of the container body 3 cooperates with the shape of the casing surface 33 and the constrictions 35, 35' of the stopper 27 such that a sealing system is created which in particular prevents flow between the inner casing surface 37 and casing surface 33 and the constrictions 35, 35' of the stopper 27 of at least two medicine substances which can be stored in the medicine container 1. Preferably, an outer diameter of the stopper 27 is greater than its inner diameter before insertion into the container body 3. The stopper 27 is thus compressed upon insertion into the container body 3.

In the embodiment of FIG. 1, an internal thread 39 is disposed on the side 31 of the stopper 27 facing away from the outlet 13, into said thread preferably a correspondingly shaped external-threaded piston can be screwed. In another preferred embodiment—not shown in FIG. 1—it is provided that no internal thread 39 is disposed on the side 31 of the stopper 27 facing away from the outlet 13. A piston can then interact with the stopper 27 on the side 31 thereof facing away from the outlet 13, in particular via a die disposed on the piston. By means of such a piston, the stopper 27 can preferably be displaced in the container body 3.

The stopper 27 has a recess 41 on its side 29 facing the outlet 13. The stopper 27 has an outer surface 43 in the region of the recess 41, the outer surface 43 having essentially the shape of an inside of a hollow hemisphere. The recess 41 is surrounded by an edge 45 on the side 29 facing the outlet 13, the edge extending between the casing surface 33 and a recess opening 47. The edge 45 has a ridge 49 here in an inner region—as seen in the radial direction. The ridge 49 extends in the direction of the outlet 13. Correspondingly, the edge 45 has an axially recessed area 50 extending in the direction of the side 31 of the stopper 27 facing away from the outlet 13—as viewed in the radial direction. In the embodiment shown here, the ridge 49 is formed not circular peripherally along the edge 45, but has four segments, wherein in FIG. 1 a first and a second segment are shown in cross section, wherein a third segment is shown in a plan view. In another preferred embodiment, the ridge 49 is circumferentially formed on the rim 45.

Furthermore, the medicine container 1 has a mixing element 51. It can be disposed in a mixing chamber in the container body 3, which is explained in more detail below. By means of the recess 41 formed on the side 29 facing the outlet 13, the stopper 27 is adapted to at least partially receive the mixing element 51. Particularly preferably, the mixing element 51 is spherical. The mixing element 51 has in particular an outer surface 52 which has a spherical shape so that the mixing element 51 can be received at least partially in the in particular hemispherical recess 41.

In the base 11 at least one first groove 53 is made, wherein in the embodiment shown here, four first grooves 53 are made in the base 11. A first and a second first groove 53 are shown in a section view in FIG. 1, wherein a third first groove is shown in a plan view. The four first grooves 53 each open into the outlet 13. In the embodiment shown here, the first grooves 53 extend substantially in the longitudinal direction of the container body 3 along the conical base 11. A width of the first grooves 53 here in the base 11 in the region of the projection 23 is wider than a width of the first grooves 53 in the base 11 in the region of the inner outlet opening 16, which is particularly easily seen in the first groove 53' shown in a plan view. With a position of the stopper 27 at the second end 7 of the container body 3, the at least two medicine substances can be discharged from the medicine container 1 through the outlet 13 at least through the at least one first groove 53, here through the four first grooves 53, 53'. Thus, when at the second end 7 of the container body 3, the mixing element 51 does not block the outlet 13, in particular not the inner outlet opening 16. Rather, a bypass is created by the first grooves 53, 53' through which the at least two medicine substances flow past the mixing element 51 and can leave the medicine container 1 through the outlet 13.

In another embodiment of the medicine container 1—not shown here—, the base 11 is formed on a separate base element together with the outlet 13, wherein the separate base element is preferably fixedly disposed on the container body 3 at the second end 7 thereof. In particular, the separate base element comprises—along the longitudinal axis 15—a portion of the container body 3 between a dashed line 55 and the outer outlet opening 17. Preferably, the container body 3—seen from the first end 5—continues beyond the line 55, wherein the container body 3 surrounds the separate base element at least partially in the circumferential direction in this area—which extends beyond line 55. There are various conceivable designs with regard to the separate base element, in which case it is ultimately important that the geometric elements shown in FIG. 1 are realized by way of the container body 3 and/or the separate base element in the region of the second end 7. It is also possible, in particular, for the container body 3 to end at line 55—as viewed from the first end 5—, wherein the region of the container body 3 shown in FIG. 1—as viewed from the first end 5—is formed above line 55 by means of the separate base element, wherein the separate base element is fixedly connected, in particular fluid-tightly, to the container body 3.

In FIG. 2, the medicine container 1 is shown schematically in a filled, closed state in a cross section. Identical and functionally-identical elements are provided with the same reference signs so that reference is made to the previous description in this regard. The stopper 27 is inserted here through the stopper opening 9 into the container body 3 and disposed at a first end 5. A mixing chamber 57 for receiving the at least two medicine substances 59 is delimited by a portion of the inner casing surface 37 of the container body 3, the side 29 of the stopper 27 facing the outlet 13, and the base 11. The inner casing surface 37 extends in particular from a contact region with the stopper 27 at the recessed area 50 up to the base 11. In the exemplary embodiment according to FIG. 2, the outlet region 14, which is delimited at the outer outlet opening 17 by a septum 61 assigned to a closure device 60, adjoins the mixing chamber 57. In the embodiment shown here, the septum 61 is fixedly disposed on the extension 19 of the container body 3 by means of a closure element 63 of the closure device 60, the closure element surrounding the septum 61. In particular, the septum 61 is held firmly by the closure element 63, in particular fluid-tightly on an edge 65 of the extension 19. The closure element 63 is crimped here in the region of the constriction 21 so that in particular it cannot be easily removed from the extension 19.

The mixing element 51 is disposed in the mixing chamber 57, wherein it is freely displaceable in the mixing chamber 57—in particular in a position of the stopper 27 according to FIG. 2—, in particular separately and independently of the stopper 27. In the embodiment according to FIG. 2, the mixing element 51 is disposed to be freely displaceable in the radial direction both along the longitudinal axis 15 and also in relation to the longitudinal axis 15. By shaking the medicine container 1, preferably by means of slight shaking movements, it is preferably possible to mix the at least two medicine substances 59 in the mixing chamber 57, wherein a mixing of the at least two medicine substances 59 is supported by a displacement of the mixing element 51 in the mixing chamber 59—in particular by way of the shaking. In the exemplary embodiment shown in FIG. 2, although the outlet region 14 is in fact fluidically connected to the mixing chamber 57, no direct support of the mixing by means of the mixing element 51 can be effected in this region since the mixing element 51 cannot penetrate into the outlet region 14, at least partially.

The medicine container 1 is adapted to discharge the at least two medicine substances 59 received in the mixing chamber 57 from the medicine container 1 through the outlet 13 by displacing the stopper 27 in the direction of the outlet 13, in particular after, for example, piercing the septum 61 by means of an injection needle, thereby creating a fluid connection between the mixing chamber 57 and the surroundings of the medicine container 1.

In FIG. 3, the medicine container 1 is shown schematically in an empty state in a cross section. Identical and functionally-identical elements are provided with the same reference signs so that reference is made to the previous description in this regard. The stopper 27 is displaced to the second end 7 in the container body 3 in accordance with FIG. 3. The displacement in the direction of the second end 7 is effected in particular using a piston 67. According to FIG. 3, the piston is fixedly connected to the stopper 27 by means of an external thread 69 which is matched to the internal thread 39 of the stopper 27. In another embodiment—not shown in FIG. 3—, the stopper 27 has no internal thread 39, wherein the piston 67 in particular has no matched external thread 69. Preferably, the piston 67 instead has a die which is adapted to apply a compressive force on the stopper 27 for axial displacement thereof.

The septum 61 is pierced here by means of an injection needle 71, wherein the injection needle 71 is placed on the closure element 63 by means of a holder 73. A fluid connection between the outlet region 14 and the surroundings of the medicine container 1 is produced by means of the injection needle 71.

From FIG. 3 it is clear that the medicine container 1 is adapted to discharge the at least two medicine substances 59 received in the mixing chamber 57 from the medicine container 1 through the outlet 13 at least partially by displacement of the stopper 27 in the direction of the outlet 13, wherein according to FIG. 3 the at least two medicine substances 59 are almost completely discharged from the medicine container 1. A volume of the mixing chamber 57 is minimized when the stopper 27 is located at the second end 7, wherein said volume substantially comprises a volume formed by the first grooves 53, 53'. The stopper 27 receives the mixing element 51 at least partially at a stopper position at the second end 7 of the container body 3. Preferably—as shown in FIG. 3—, a shape of the outer surface 43 of the stopper 27 in the region of the recess 41 is matched to a shape of the outer surface 52 of the mixing element 51 in such a way that, when the stopper 27 reaches over the mixing element 51 maximally by means of the recess 41 no cavity remains between the outer surface 43 of the stopper 27 in the region of the recess 41 and the outer surface 52 of the mixing element 51. In this way, a dead volume of the at least two medicine substances 59 which cannot be discharged from the medicine container 1 is reduced, in particular even when the stopper 27 is displaced up to the second end 7. In the embodiment shown in FIG. 3, the stopper 27 reaches about half of the way over the mixing element 51 by means of the recess 41.

Preferably—as shown in FIG. 3—, the stopper 27 rests on the base 11 in some areas when the stopper is located at the second end 7 of the container body 3. In particular, the edge 45 of the stopper 27 rests on the projection 23. In particular, the recessed area 50 of the edge 45 rests on the projection 23, wherein the ridge 49 of the edge 45 projects laterally outward beyond the projection 23. In this way, the dead volume of the at least two medicine substances 59 is significantly reduced.

It can be seen that in a position of the stopper 27 at the second end 7, the mixing element 51 is substantially fixedly disposed between the outer surface 43 of the stopper 27 and the base 11. The mixing element 51 is in particular disposed such that a cavity is avoided between the outer surface 52 of the stopper 27 in the region of the recess 41 and the outer surface 43 of the mixing element 51. Through the first grooves 53, 53', the at least two medicine substances 59 can be discharged from the medicine container 1 through the outlet 13, wherein the at least two medicine substances 59 flow along the arrows P through the first grooves 53, 53', in particular past the mixing element 51.

It can be seen that in the exemplary embodiment according to FIG. 3 only a minimal dead volume of the at least two medicine substances 59 remains, which is located in particular in the outlet region 14 and the first grooves 53, 53', provided that the at least two medicine substances 59 do not flow by themselves from the medicine container 1 flow. In a further preferred embodiment of the medicine container 1—not shown here—, the septum 61 projects in the direction of the inner outlet opening 16, wherein the dead volume in the outlet region 14 is significantly reduced.

In a further preferred embodiment of the medicine container 1, at least one second groove 70 is made in the outer surface 52 of the mixing element 51, wherein at a position of the stopper 27 at the second end 7 of the container body 3 the at least two medicine substances 59 can be discharged from the medicine container 1 through the outlet 13 at least through the at least one second groove.

Particularly preferably, the shape of the outer surface 52 of the mixing element 51 is adapted to a shape of the base 11 such that in a position of the stopper 27 at the second end 7 of the container body 3, no cavity remains between the outer surface 52 of the mixing element 51 and the base 11 in an area outside the at least one first groove 53, 53' and/or second groove—not shown here.

As shown in the simplified view of FIG. 4, in a further preferred embodiment of the medicine container 1, the mixing chamber 57 is formed as a first chamber of a medicine container 1 designed as a double-chambered carpule. Preferably, the stopper 27 separates the mixing chamber 57 from a second chamber 57' of the medicine container 1, which is disposed in the container body 3 and is designed as a double-chambered carpule. The second chamber 57' is preferably disposed between the first end 5 of the container body 3 and a side of the stopper 27 facing the stopper opening 9, that is to say the side 31 of the stopper 27 facing away from the outlet 13.

Below, a method for operating a medicine container 1 will be described, wherein the medicine container 1 comprises a container body 3, a stopper 27 and a mixing member 51. In particular, a medicine container 1 according to one of the embodiments described above is operated by means of the method, the method being carried out in particular using the medicine container 1 according to one of the embodiments described above. In the process, the stopper 27 inserted into the container body 3 is displaced along the longitudinal axis 15 of the container body 3 toward the outlet 13 of the container body 3 located at the second end 7 of the container body 3 so as to discharge the at least two intermixable medicine substances 59 located in the mixing chamber 57 of the medicine container 1 from the medicine container 1 through the outlet 13 at least partially. By means of the stopper 27, the mixing element 51 disposed in the mixing chamber 57 is at least partially received in the recess 41 which is formed on the side 29 of the stopper 27 facing the outlet 13 when the stopper is located in a position at the second end 7 of the container body 3. Preferably, the mixing element 51 is at least partially already received by the stopper 27 by means of the recess 41—in particular after the at least two medicine substances 59 have been mixed together—, before the stopper 27 rests against the second end 7. Particularly preferably, the mixing element 51 is not jammed in the stopper 27 in the region of the recess 41, so that in particular in a multiple application of the at least two medicine substances 59, mixing the at least two medicine substances 59 can be effectively at least supported by means of the mixing element 51 even when the stopper 27 is located between the first end 5 and the second end 7.

Overall, it can be seen that by means of the medicine container 1 and the method for operating the medicine container 1 a discharge behavior of the medicine container 1 can be significantly improved. In particular, effective mixing of the at least two medicine substances 59 by the mixing element 51 is at least supported, in particular when shaking the medicine container 1. In addition, a dead volume of the at least two medicine substances 59 which may remain in the medicine container 1 is effectively minimized. In particular, highly viscous medicine substances 59 can also be easily and safely discharged from the medicine container 1 through the outlet 13 by means of the at least one first groove 53, 53' and/or second groove.

The invention claimed is:

1. A medicine container for storing and providing at least two intermixable medicine substances, the medicine container comprising:
   a container body, the container body having a first end and a second end opposite the first end, the first end defining a stopper opening and the second end having a base with an outlet;
   a stopper insertable into the container body through the stopper opening and displaceable in the container body along a longitudinal axis of the container body between the first and second ends, a side of the stopper facing the outlet and the base;
   a mixing chamber for receiving the at least two intermixable medicine substances, the mixing chamber delimited by a section of an inner casing surface of the container body; and
   a mixing element disposed in the mixing chamber,
   wherein the medicine container is adapted to at least partially discharge the at least two intermixable medicine substances received in the mixing chamber from the medicine container through the outlet by displacement of the stopper toward the outlet,
   wherein the stopper is adapted to receive the mixing element at least partially by a recess formed on the side of the stopper facing the outlet when the stopper is disposed at the second end of the container body,
   wherein the base includes at least two first grooves opening into the outlet, wherein at a position of the stopper at the second end of the container body the at least two intermixable medicine substances are dischargeable from the medicine container through the outlet at least through the at least two first grooves,
   wherein the outlet is disposed, with respect to the longitudinal axis of the container body, in a central region of the base, and
   wherein the recess and the outlet are formed in alignment with each other.

2. The medicine container according to claim 1, wherein a shape of an outer surface of the stopper in a region of the recess is adapted to a shape of an outer surface of the mixing element such that when the mixing element maximally reaches over the stopper by the recess no cavity remains between the outer surface of the stopper in the region of the recess and the outer surface of the mixing element.

3. The medicine container according to claim 1, wherein the stopper partially rests on the base in a position thereof at the second end of the container body.

4. The medicine container according to claim 1, wherein an outer surface of the mixing element includes at least one second groove, and wherein with a position of the stopper at the second end of the container body the at least two intermixable medicine substances are dischargeable from the medicine container through the outlet at least through the at least one second groove.

5. The medicine container according to claim 4, wherein a shape of the outer surface of the mixing element is matched to a shape of the base so that, in a position of the stopper at the second end of the container body no cavity remains between the outer surface of the mixing element and the base in an area outside the at least one first and/or second groove.

6. The medicine container according to claim 1, wherein the base is formed with the outlet on a separate base element disposed on the container body at the second end of the container body.

7. The medicine container according to claim 1, wherein the mixing element is spherical.

8. The medicine container according to claim 1, wherein:
the mixing chamber is designed as a first chamber of a medicine container designed as a double-chambered carpule,
the stopper separates the mixing chamber from a second chamber of the medicine container disposed in the container body thereof, the medicine container being designed as a double-chambered carpule, and
the second chamber is disposed between the first end of the container body and the side of the stopper facing away from the outlet.

9. A method for operating a medicine container according to claim 1, the method comprising:
inserting the stopper into the container body and displacing the stopper along the longitudinal axis of the container body in a direction of the outlet of the container body located at the second end of the container body to discharge at least two medicine substances that can be mixed with one another in the mixing chamber of the medicine container from the medicine container through the outlet,
wherein the mixing element disposed in the mixing chamber is at least partially received in the recess formed in the side of the stopper facing the outlet by way of the stopper in a position thereof at the second end of the container body.

10. The method for operating a medicine container of claim 9, further comprising discharging the at least two intermixable medicine substances from the medicine container through the outlet at least through the at least two first grooves.

* * * * *